(12) United States Patent
Rhaodes

(10) Patent No.: US 7,638,144 B2
(45) Date of Patent: *Dec. 29, 2009

(54) COMPOSITION, APPARATUS AND METHOD FOR SKIN REJUVENATION

(75) Inventor: Dean Rhaodes, Beverly Hills, CA (US)

(73) Assignee: DermaNew, Inc., Beverly Hills, CA (US)

(*) Notice: Subject to any disclaimer, the term of this patent is extended or adjusted under 35 U.S.C. 154(b) by 186 days.

This patent is subject to a terminal disclaimer.

(21) Appl. No.: 09/802,425

(22) Filed: Mar. 9, 2001

(65) Prior Publication Data

US 2001/0018061 A1  Aug. 30, 2001

Related U.S. Application Data

(63) Continuation-in-part of application No. 09/411,712, filed on Oct. 4, 1999, now Pat. No. 6,652,888.

(51) Int. Cl.
*A61K 33/06* (2006.01)
*A61K 8/02* (2006.01)
*A61K 47/00* (2006.01)

(52) U.S. Cl. .................. 424/691; 424/401; 514/769; 514/770

(58) Field of Classification Search ............. 424/401, 424/691; 514/769, 770
See application file for complete search history.

(56) References Cited

U.S. PATENT DOCUMENTS

| | | | |
|---|---|---|---|
| 1,653,901 A | 12/1927 | Haessly | |
| 2,985,166 A | 5/1961 | Burkardt | |
| 3,092,111 A * | 6/1963 | Saperstein | 606/131 |
| 3,852,417 A * | 12/1974 | McLaughlin | 424/47 |
| 4,284,533 A | 8/1981 | Imamura et al. | |
| 4,957,747 A | 9/1990 | Stiefel | |
| 4,992,476 A | 2/1991 | Geria | |
| 5,219,571 A * | 6/1993 | Wise | 424/401 |
| 5,360,824 A | 11/1994 | Barker | |
| 5,607,980 A * | 3/1997 | McAtee et al. | 514/476 |
| 5,679,877 A | 10/1997 | Erilli et al. | |
| 5,753,245 A | 5/1998 | Fowler et al. | |
| 5,756,081 A * | 5/1998 | Wdowik | 424/73 |
| 5,800,446 A | 9/1998 | Banuchi | |
| 5,891,449 A | 4/1999 | Daniel et al. | |
| 6,010,268 A | 1/2000 | Sereg et al. | |
| 6,090,085 A | 7/2000 | Mehl et al. | |
| 6,139,553 A | 10/2000 | Dotan | |
| 6,290,976 B1 | 9/2001 | Messenger | |
| 6,294,179 B1 * | 9/2001 | Lee et al. | 424/401 |
| 2002/0090385 A1 * | 7/2002 | Fox et al. | 424/401 |

FOREIGN PATENT DOCUMENTS

| | | |
|---|---|---|
| DE | 27 18 158 A | 11/1978 |
| EP | 0 336 900 A | 10/1989 |
| EP | 0 571 193 A | 11/1993 |
| FR | 2 564 318 A | 11/1985 |
| GB | 1 021 276 A | 3/1966 |
| WO | WO 92 21306 A | 12/1992 |
| WO | WO 97/22325 | 6/1997 |
| WO | WO 99/21532 | 6/1999 |

OTHER PUBLICATIONS

The American Heritage Dictionary of the English Language (4th Ed. 2000)[online],"moisturizer" [retrieved on Jul. 22, 2003]. Retrieved from the internet <URL:http://www.bartleby.com/61/4/M0370450.html>.*
Merriam-Webster's Collegiate Dictionary (10th Ed. 1998), pp. 272,749.*
Epoxy Definitions (2002), www.primeresins.com/onlineresources/epoxy_definitions.php.*

* cited by examiner

Primary Examiner—Sreeni Padmanabhan
Assistant Examiner—Frank I Choi
(74) Attorney, Agent, or Firm—Blakely, Sokoloff, Taylor & Zafman, LLP

(57) ABSTRACT

A composition including a base and a plurality of abrasive particles. An apparatus including a head, and an applicator coupled to the head, the applicator having dimensions suitable for contacting localized areas of human skin. A method including applying a composition to an area of human skin, the composition comprising a base and a plurality of abrasive particles, and manipulating the composition over the area of human skin with a handle-operated instrument.

2 Claims, 4 Drawing Sheets

COMPOSITION, APPARATUS AND METHOD FOR SKIN REJUVENATION

CROSS-REFERENCE TO RELATED APPLICATION

The application is a Continuation-In-Part of application Ser. No. 09/411,712, filed Oct. 4, 1999 by Applicant, Dean Rhodes, entitled "Method for Skin Rejuvenation with Buffing Creme" issued as U.S. Pat. Ser. No. 6,652,888 on Nov. 25, 2003.

FIELD OF THE INVENTION

The invention relates to skin treatment.

BACKGROUND

Facial skin rejuvenation has been accomplished by chemical treatment referred to as "chemical peels" or laser treatment referred to as "laser surgery" and exfoliation by machine driven means, such as with emery paper. Such methods generally require medical supervision and involve some risk of deleterious side effects as well as pain and discomfort during treatment. These methods all require long recovery time between treatments.

Microdermabrasion (e.g., microexfoliation, particle skin resurfacing) is a technique in skin care in which a controlled exfoliation of the skin is performed to improve and remove skin abnormalities. A typical microdermabrasion machine consists of a compressor to project inert crystals of corundum (aluminum oxide or alumina) through a tube into a hand piece manipulated by a technician over the skin of the subject. The compressor projects the corundum across the skin with variable pressure while the hand piece is in contact with the skin. This induces an abrasion action which removes the top layer of skin. At the same time, through another tube within the hand piece, the used corundum and abraided skin are vacuumed into another container for disposal. As can be appreciated, the need for the compressor, the supply of corundum, and a vacuum source and disposal container are suitable for a specialty clinic with trained technicians.

What is desired is an inexpensive method that may be safely applied upon a human subject's own skin to achieve the desired rejuvenation without pain or discomfort during treatment.

DETAILED DESCRIPTION

Figure 1:
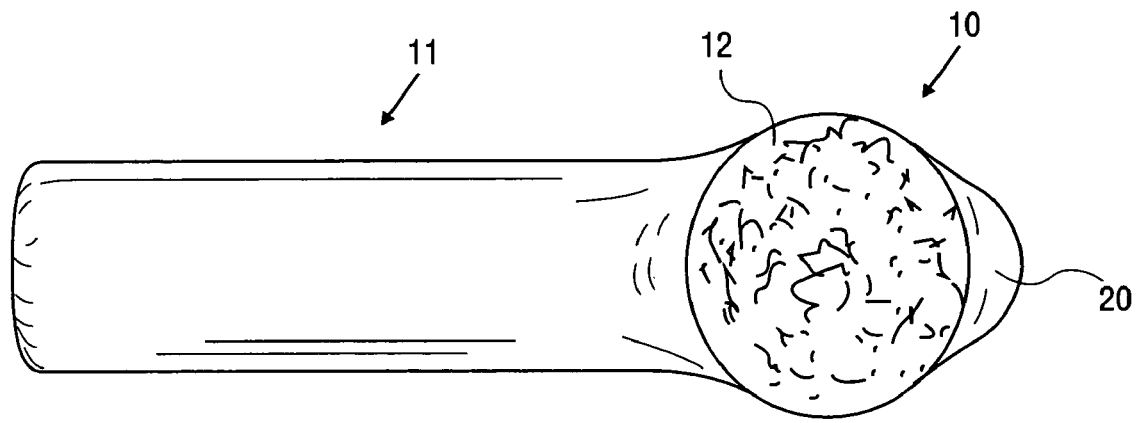
FIG. 1 is a plan view of a portable applicator apparatus having a snap-on disk with an applicator pad coupled to a portion of the apparatus in accordance with an embodiment of the invention.

A composition is disclosed including a base and a plurality of abrasive particles. In one aspect, the composition includes a base comprising as a principal component a moisturizer suitable for application to the human skin and a plurality of abrasive particles. Suitable abrasive particles include inorganic particles such as corundum, aluminum oxide, alumina, $Al_2O_3$ and magnesium oxide (MgO). In one embodiment, the abrasive particles are microcrystals of corundum having an average particle size on the order of 34 microns (μm) to 556 μm (320 to 30 grit). More preferably, the average particle size of the microcrystals is on the order of about 42 μm to 198 μm (280 to 60 grit).

The abrasive nature of the particles in the composition render the composition suitable as an exfoliator to improve the look and feel of an area of human skin and remove skin abnormalities. More specifically, the abrasive particles tend to remove the outer layer of skin (the epidermis) to expose an underlayer of skin. The human body responds by producing a new layer of skin. With one or more (and preferably a series) of these exfoliation treatments, it is believed that the skin subject to the treatment may be improved. Such improvements include improvement in the appearance of fine lines, wrinkles, stretch marks, non-inflammatory acne, acne scars, surgical scars, rough or coarse textured skin, age spots, blotchy skin conditions, and sun damaged skin.

In one embodiment, the composition comprises a base that is capable of suspending the plurality of abrasive particles within the base. One particular component, that in one embodiment is included as a principal component in the base, is a moisturizer. Moisturizers are believed to reduce water loss from the skin and draw moisture from inner skin layers up into the outer skin layer. In this regard, in one embodiment, the moisturizer includes a substance that attracts moisture to the top skin layer (a humectant). Suitable humectants include glycerin, propylene glycol, alpha hydroxy acids, urea, and lactic acid. The moisturizer may also include substances that tend to reduce water loss by creating a barrier. Such substances include petrolatum, mineral oil, lanolin and silicone derivatives.

Suitable moisturizers may be in various forms as known in the art. Such forms include but are not limited to, liquids, including but not limited to, creams, gels, pastes and emolients. In addition to the moisturizer, the base of the composition may further include, but is not limited to, antioxidants, aromas/fragrances, vitamins (particularly vitamins A, C and E), emulsifiers, toners, acids (e.g., glycolic acid), scrubs, serums, lotions, liquids, elixirs, sun screens, and tonics.

In another embodiment, the base of the composition is a liquid including a cleansing component, including, but not limited to, soaps, salicylic acid, a lauryl sulfate (e.g. sodium lauryl sulfate or sodium laureth sulfate). The cleansing component base may also be combined with a moisturizer. Other components such as surfactants and emulsifiers may further be included. Antimicrobial or bactericidal agents may still further be included. An example of a suitable composition is a composition comprising 20 to 70 percent by weight corundum, 20 to 70 percent aloe gel, and five to 20 percent sodium lauryl sulfate. A thickening agent may also be added where desired.

In one embodiment, abrasive particles of corundum (alumina) microcrystals are combined with a creme moisturizer base in an amount of about 5 to 100 grams of corundum per ounce of creme, preferably 10 to 50 grams per ounce, and more preferably 10 to 20 grams per ounce.

The abrasive articles suspended in the cream moisturizer provide a gentle microdermabrasion of the skin for resurfacing/rejuvenating the skin, leaving it smooth and soft after each treatment without the need of any recovery time so that it may be repeated as often as on a daily basis, in order to reduce and erase fine lines and wrinkles, reduce pore size, reduce or erase sun damage, age spots and skin discoloration, firm skin and muscle tone, thereby to reduce sagging, enhance new epidermal cells and decongest acne skin conditions. This method of rejuvenating the skin, and particularly the facial skin, is ideal for those unwilling or unable to undergo laser surgery, a chemical peel, or machine driven exfoliation.

One example of a suitable composition including corundum (alumina) microcrystals and a cream moisturizer at approximately 14 grams microcrystals per ounce of cream includes:

| Ingredients | Percentage |
| --- | --- |
| Aluminum Oxide | 35.000 |
| Purified Water | 14.288 |
| Caprylic/Capric Triglyceride | 11.500 |
| Octyl Palmitate | 10.000 |
| Safflower Oil | 10.000 |
| Cetearyl Alcohol | 3.000 |
| Sodium Cetearyl Sulfate | 2.100 |
| Stearic Acid | 5.000 |
| Wheat Germ Oil | 3.000 |
| Propylene Glycol | 2.900 |
| Panthenol | 1.000 |
| Lecethin | 0.500 |
| Cetyl Alcohol | 0.500 |
| Tocopheryl Acetate (vitamin E) | 0.100 |
| Retinyl Palmitate (vitamin A) | 0.100 |
| Ascorbyl Palmitate | 0.100 |
| Extract of Carrot | 0.050 |
| Wheat Germ | 0.050 |
| Wheat Bran | 0.050 |
| Aminomethyl Propanediol | 0.050 |
| Beta Carotene | 0.010 |
| Methylparaben | 0.200 |
| Propylparaben | 0.100 |
| Phenoxyethanol | 0.200 |
| FDC Yellow 5 | 0.001 |
| FDC Yellow 6 | 0.001 |
| Fragrance | 0.200 |

In one embodiment, the composition is provided in a jar (not shown) having a mouth large enough for an applicator of the applicator apparatus described below to be dipped into the composition in the jar. Alternatively, the composition may be scooped out of the jar by hand and applied to the skin area to be treated. Pump mechanisms or squirt bottle tube configurations for dispensing the compositions are also suitable.

In another embodiment, an apparatus is disclosed. A suitable apparatus includes a portable device having a vibrating head and an applicator coupled to the vibrating head. The applicator has dimensions suitable for contacting localized areas of human skin.

Figure 2:
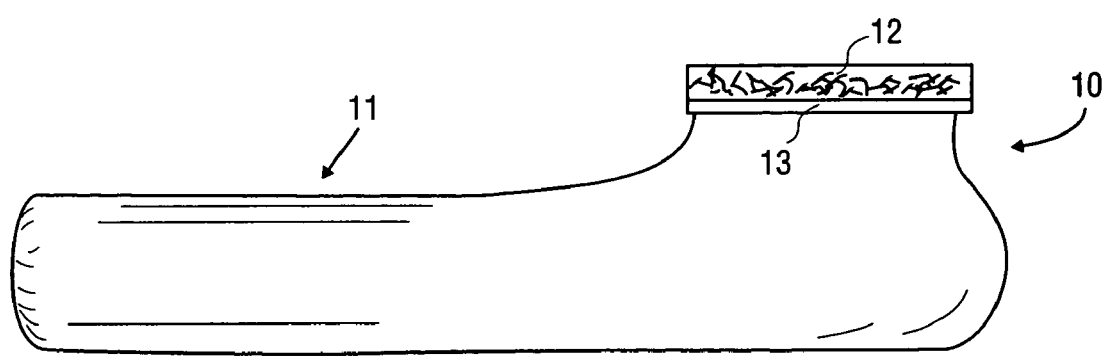
FIG. 2 is a side view of the apparatus of FIG. 1.

Referring to FIGS. 1 and 2, a powered (dc battery or ac power driven) applicator apparatus (vibrator) including a vibrating device encased in head portion 10 of the apparatus (vibrator) housing. The apparatus (vibrator) also includes handle portion 11 which is adapted to house in an interior volume, a removable/replaceable power source, such as batteries (e.g., multiple AA batteries), optional circuitry for coupling to an AC power source, and circuitry to operate a motor (e.g., DC) driven apparatus (vibrator). The apparatus, in one embodiment, is formed of a plastic formed casing.

The apparatus (vibrator) also includes applicator 12 coupled to head portion 10 of the apparatus (vibrator). Applicator 12 is a porous material such as a cloth or sponge having dimensions suitable for contacting an area of human skin, for example, a sponge pad, e.g., a polyurethane sponge pad, a latex sponge pad, or other closed-cell sponge material. One suitable sponge material is commonly referred to as "makeup" sponge material used representatively in the makeup arts. Other open-celled sponge material may also be used. Alternatively, applicator 12 is a non-porous material such as synthetic rubber, plastic or latex.

Figure 3:
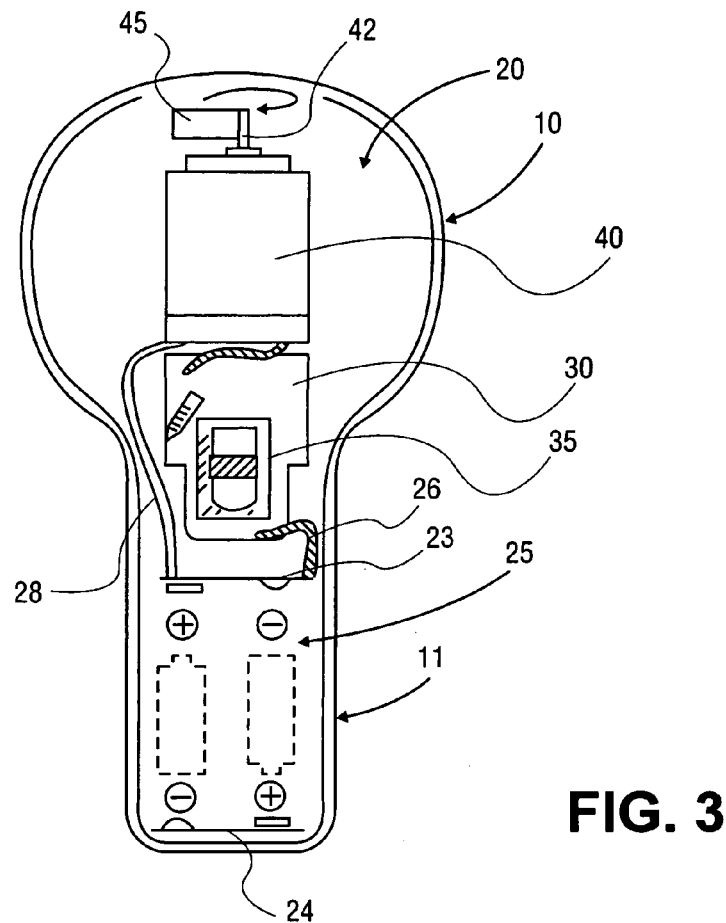
FIG. 3 is a cross-sectional back side view of the apparatus of FIG. 1.

FIG. 3 shows a schematic cross-sectional view of an embodiment of the apparatus of FIG. 1, specifically the vibrator portion of the apparatus. In cross-section, the operation of the vibrating mechanism is described. The apparatus (vibrator) includes, in this embodiment, a removable power source. In this case, the apparatus (vibrator) includes handle portion 11 having interior chamber 25 to accommodate the removable power source. In one example, the power source to operate the vibrator is two AA batteries that fit within interior chamber 25 of handle portion 11. Conductors 23 and 24 define ends of the interior chamber. Leads 26 and 28 coupled to conductor 23 bring current to/from motor 40. Lead 26 is coupled to circuit board 30 that includes switch 35 to control the operation of motor 40. Switch 35 may be a two-position switch (ON/OFF) or a multiple position switch for operating motor 40 at multiple speeds.

Motor 40 is disposed in an interior portion 20 of head portion 10 of vibrator 10 and includes shaft 42 extending from one end of motor 40. Shaft 42 is rotated (as illustrated) with the operation of motor 40.

Coupled to an end of shaft 42 of motor 40 is eccentric mass 45. In this embodiment, eccentric mass 45 is a semi-cylindrical body coupled at its axis to post 42. In this manner, as eccentric mass 45 rotates, its shape generates a rhythmic motion in head portion 10 of the apparatus (vibrator) producing a vibration.

Figure 4:
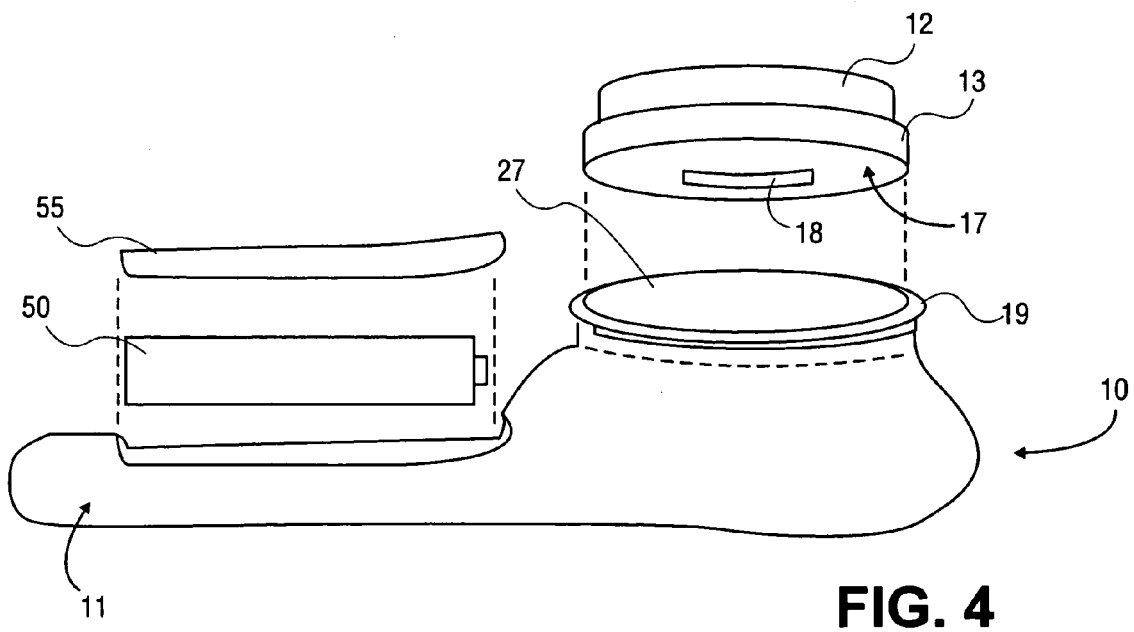
FIG. 4 is a top side perspective exploded view of the apparatus of FIG. 1.

FIG. 4 shows an exploded side view of the apparatus of FIG. 1. The vibrator includes handle portion 11 that is sized in one portion to be grasped by a human subject. Handle portion 11 includes interior volume 25 for accommodating a removable/replaceable power source, such as one or more batteries 50 (e.g., two AA batteries). Cover 55 snaps into the body of handle portion 11 to enclose the power source within the interior volume of handle portion 11.

FIG. 4 also shows the configuration of applicator 12 to head portion 10 of the apparatus (vibrator). In one embodiment, applicator 12 is coupled to cap 13 (such as by an adhesive between applicator 12 and one surface of cap 13). Cap 13, as illustrated, is a circular body having a diameter similar to the diameter of vibrating head 27 of head portion 10 of the vibrator.

In one embodiment, vibrating head 27 has a diameter on the order of about one to two inches (about 2.5-5 centimeters). In one embodiment, the diameter of vibrating head 27 is slightly larger on the order of, for example, 0.01 to 0.03 inches (1-2 millimeters) then the main body of head portion 10 as represented by lip 19.

An underside of cap 13 has interior volume 17. One or more protrusions 18 extend from the side walls of cap 13 (defining interior volume 17) so that cap 13 does not fit easily over lip 19 of head portion 10. Cap 13 is made of a thin plastic material, in one embodiment, which allows the cap to be deformed and snapped over lip 19, vibrating head 27, and onto head portion 10 to securely hold cap 13 in place. Alternatively, the cap may have a groove that snaps over a ridge around the inside wall of the head.

Applicator 12, which is secured to the top of cap 13 may be replaced after many uses. In one embodiment, applicator 12 and cap 13 may be removed from the apparatus after use and cleaned. When it is considered to be no longer useful after, for example, one or more cleanings, applicator 12 (and cap 13) may be discarded and replaced.

Figure 5:
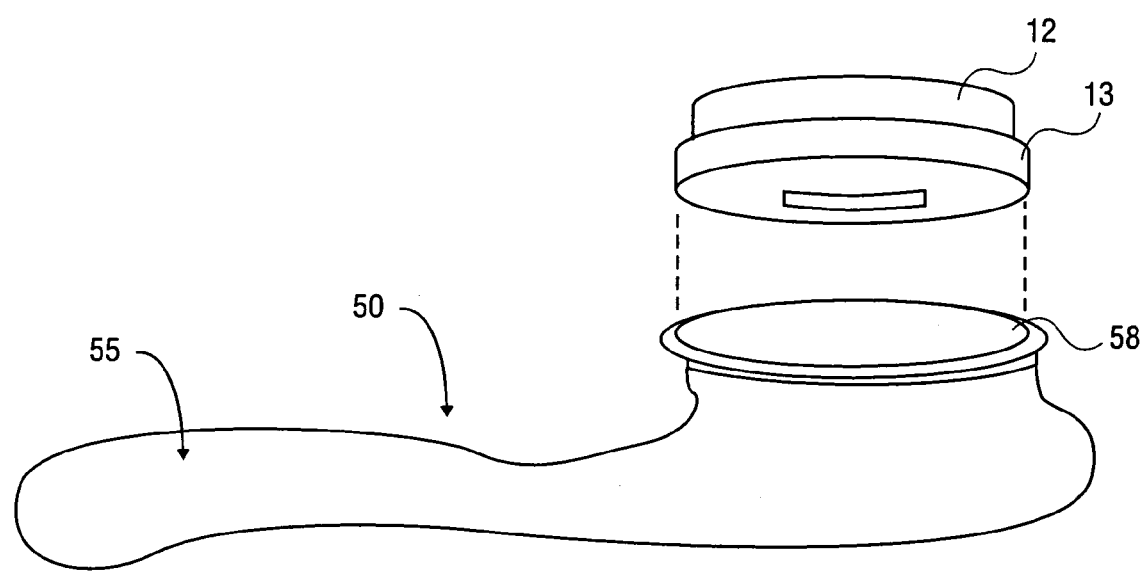
FIG. 5 is a top side perspective exploded view of a second embodiment of an apparatus in accordance with the invention.

In the embodiment described with reference to FIGS. 1 through 4, an apparatus including a vibrating mechanism is described. It is believed that in applying a composition to an area of human skin and manipulating the composition with a vibrating apparatus, as described with reference to FIG. 6 and the accompanying text, the vibrating action of the apparatus (e.g., of the applicator) helps stimulate skin, muscle, and tissue to revitalize the treated area. It is appreciated that, in use, the vibrating mechanism may or may not be used. In this regard, FIG. 5 shows another embodiment of a manually-manipulated or operated apparatus. Apparatus 50 includes handle 55 suitable for gripping by a hand of a human subject. Handle 55 includes, at one end, head portion 58 having dimensions suitable for accommodating cap 13 and applicator 12 in a manner similar, in one embodiment, to the manner described with reference to FIGS. 1 through 4.

Figure 6:
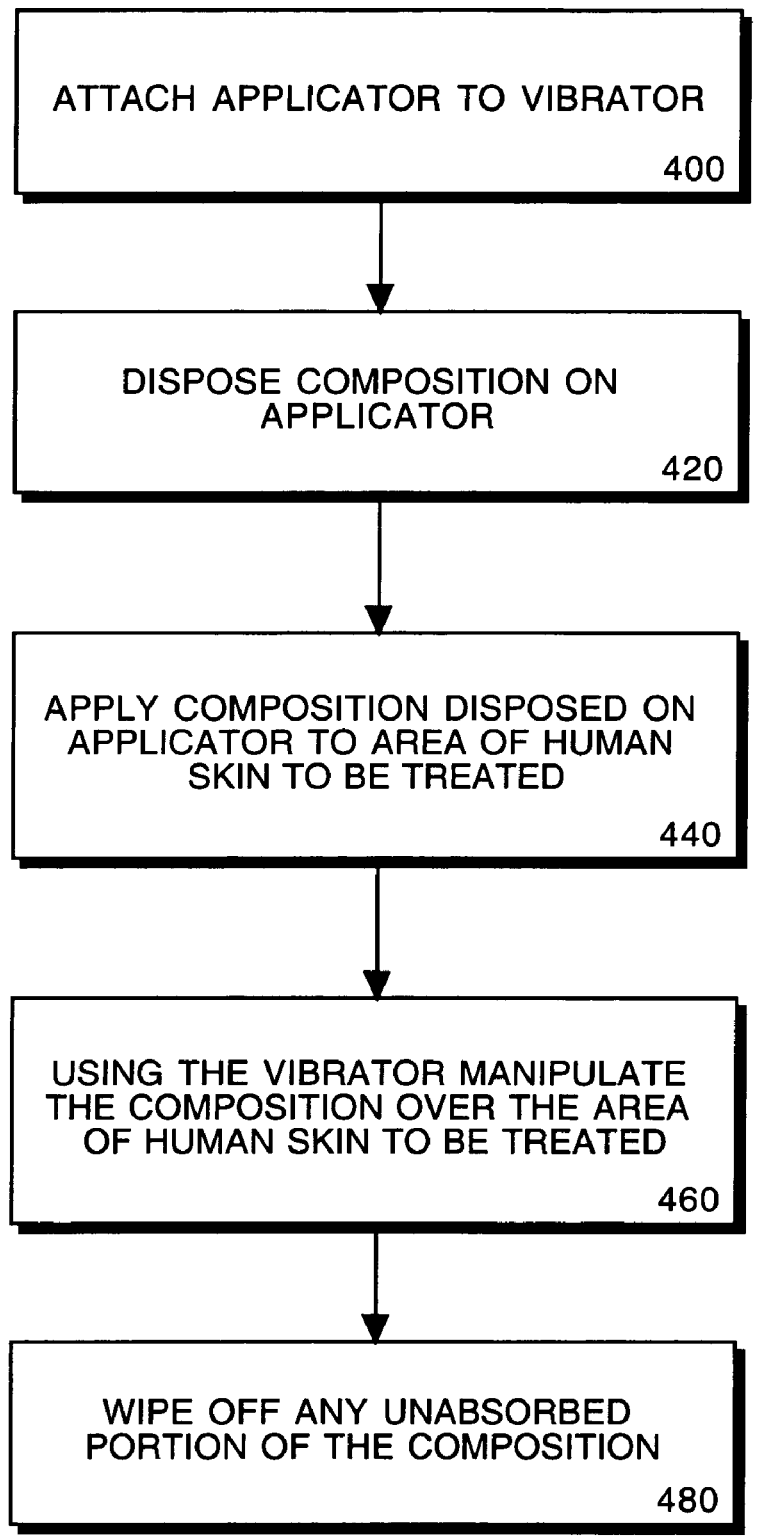
FIG. 6 is a flow chart describing an operation to treat skin according to an embodiment of the invention.

FIG. 6 shows a flow chart illustrating practicing a method utilizing either the apparatus comprising the motor-driven vibrating mechanism or the manually-manipulated device. Initially, a human user attaches an applicator to the apparatus (vibrator) (block 400). Next, the composition of, for example, moisturizer and abrasive particles, is disposed on the applicator (block 420). This can be accomplished either by dipping the applicator into a container with the composition disposed inside or by disposing the composition directly onto the applicator (i.e., with a dispenser, a squirt bottle tube, spatula or other suitable means). The user then applies the composition disposed on the applicator to the area of skin to be treated (block 440). On example is applying approximately one-quarter inch of the composition across the entire surface of a porous applicator. The user then dots the area to be treated at locations on the order of, for example, three inches apart. Subsequently, the user manipulates the composition over the area of skin to be treated with the apparatus (vibrator) (block 460). In an embodiment, manipulation of the composition (block 460) is characterized by moving the apparatus (vibrator) over the area of skin using firm, upward, circular strokes. In one example, the manipulation of the composition is continued for one to ten minutes or until the composition has been worked into the skin and the skin appears soft and smooth.

Finally, the user wipes off any unabsorbed portion of the composition (block 480) and may optionally rinse or cleanse the area. In one embodiment, the composition comprising a moisturizer as a principal component may be worked in until substantially all of the moisturizer (and any other components) is taken up by the skin and only the corundum remains on the surface of the skin. The corundum may be brushed off and the area of skin cleansed with a mild cleanser. In an alternative embodiment, before applying the composition to the skin, the user cleanses the area of skin with a mild cleanser using gentle circular strokes, rinses the skin with tepid water, and pat the skin dry with a soft towel.

It should be noted that in applying the composition to the skin 440, the user may dab the composition on certain areas of the skin before switching the apparatus (vibrator) on to manipulate the composition over the skin. Alternatively, the user may simultaneously apply the composition to the skin and manipulate the composition over the area of skin to be treated. Alternatively, the user may simultaneously apply the composition to the applicator, dot the area to be treated and manipulate in rotary strokes. Using the vibrator applicator, the user may manipulate the applicator with the vibrator in the on (vibrate) position, or in the off position for a lighter treatment.

Other formulations of suitable compositions may occur to those skilled in the art which, upon suspending abrasive particles in the base in accordance with the invention, would be within the scope of the following claims.

What is claimed is:

1. A composition comprising:
    a base in the form of a cream suitable for application to human skin; and
    a plurality of particles of corundum suspended in the base having an average particle size from 34 to 124 microns, and
    wherein the plurality of particles of corundum are at least thirty five percent by weight of the compositions.

2. The composition of claim 1, further comprising at least one of a vitamin, a mineral, an antioxidant, a cleanser, and an emulsifier.

* * * * *

UNITED STATES PATENT AND TRADEMARK OFFICE
CERTIFICATE OF CORRECTION

| | | |
|---|---|---|
| PATENT NO. | : 7,638,144 B2 | |
| APPLICATION NO. | : 09/802425 | |
| DATED | : December 29, 2009 | |
| INVENTOR(S) | : Dean Rhoades | |

It is certified that error appears in the above-identified patent and that said Letters Patent is hereby corrected as shown below:

On the Title Page, in Item [12], please correct the spelling of the Inventor's last name to -- Rhoades--.

On the Title Page, in Item [75], under Inventor, please delete "Rhaodes" and insert --Rhoades--.

Signed and Sealed this
Second Day of August, 2011

David J. Kappos
*Director of the United States Patent and Trademark Office*